United States Patent [19]

Weisrock

[11] 4,377,637

[45] Mar. 22, 1983

[54] METHOD FOR PRODUCING A LOW VISCOSITY XANTHAN GUM

[75] Inventor: William P. Weisrock, Broken Arrow, Okla.

[73] Assignee: Standard Oil Company (Indiana), Chicago, Ill.

[21] Appl. No.: 319,485

[22] Filed: Nov. 9, 1981

Related U.S. Application Data

[63] Continuation-in-part of Ser. No. 214,804, Dec. 8, 1980, abandoned.

[51] Int. Cl.$^3$ ............................................. C12P 19/06
[52] U.S. Cl. ................................................. 435/104
[58] Field of Search ........................................ 435/104

[56] References Cited

FOREIGN PATENT DOCUMENTS 2008138 5/1979 United Kingdom .

OTHER PUBLICATIONS

Cadmus et al. in Biotechnology and Bioengineering, vol. XX, pp. 1003–1014 (1978).
Silman et al., Biotechnology and Bioengineering, vol. XII, pp. 75–83 (1970).
Davidson, FEMS Microbiology Letters, pp. 347–349 (1978).

Primary Examiner—Lionel M. Shapiro
Attorney, Agent, or Firm—Stephen R. May; Fred E. Hook

[57] ABSTRACT

In the production of xanthan gum by action of the Xanthomonas bacteria on a nutrient medium, a low viscosity xanthan gum is produced by adding sulfate anions in a concentration ranging from about 0.2 to about 0.5 wt % of the nutrient medium during the culture of the Xanthomonas bacteria in the nutrient medium. A reduced viscosity xanthan gum is produced which can be converted to the normal viscosity xanthan gum.

12 Claims, No Drawings

METHOD FOR PRODUCING A LOW VISCOSITY XANTHAN GUM

RELATED U.S. APPLICATION DATA

This application is a continuation-in-part of Ser. No. 214,804, filed Dec. 8, 1980, now abandoned.

INTRODUCTION

The present invention relates to a method for producing a reduced viscosity heteropolysaccharide, such as xanthan gum, by action of bacteria of the genus Xanthomonas on suitable nutrient media. More particularly, it is concerned with production of a low viscosity xanthan gum, which can be converted to a normal viscosity xanthan gum by conventional processes.

BACKGROUND OF THE INVENTION

Fermentation of an inoculated medium with Xanthomonas organisms for 36 to 72 hours under aerobic conditions results in the formation of xanthan gum, which is separated from other components of the medium by precipitation with acetone or methanol in a known manner. Because of the time required to ferment each batch, the low biopolymer content of the fermented medium and the processing steps including agitation required for production, recovery and purification of the product, xanthan is relatively expensive. Earlier work has indicated that the heteropolysaccharide produced by the action of Xanthomonas bacteria on carbohydrate media have potential application as film forming agents, as thickeners for body building agents in edible products, cosmetic preparations, pharmaceutical vehicles, oil field drilling fluids, fracturing liquids, and emulsifying, stabilizing and sizing agents. Heteropolysaccarides, particularly xanthan gum, have significant potential as mobility control agents in micellar polymer flooding. Xanthan gum has excellent viscosifying properties at low concentration. It is resistant to shear degradation, and exhibits only minimal losses in viscosity as a function of temperature, pH, and ionic strength. For these reasons, it is an attractive alternative to synthetic polyacrylamide for enhanced oil recovery operations.

However, in order for xanthan gum to be used in enhanced oil recovery operations as a mobility control agent, the cost must be sufficiently low to make such operations economical. It has been shown that the economics of xanthan fermentation are sensitive, at least in part, to the amount of energy necessary for mass transfer of oxygen, i.e., agitation of the fermenting medium. Mass transfer of oxygen to the growing cells is necessary, since approximately 1.5 grams of oxygen from the air is required to produce about 1 gram of cells and about 0.3 grams of oxygen is required to produce about 1 gram of xanthan gum.

Supply of the oxygen is accomplished through application of vigorous agitation to the viscous aerated fermentation broth. Experimental fermentations have demonstrated that more viscous systems require more agitation to maintain oxygen concentrations in the liquid above zero. Economic studies have shown that the cost of providing agitation amounts to between 10% and 30% of the total xanthan broth product cost. Any process improvements which enhance this mass transfer will improve the overall economics. Therefore, it would be advantageous to produce xanthan at normal concentrations in a fermentation, but with reduced viscosity, so as to lower mass transfer requirements. For example, in a normal fermentation process, reducing the viscosity of the xanthan gum broth from 4000 to 2000 cp can lower the per pound price of xanthan by as much as 10%.

Low viscosity xanthan is useful in certain fluid applications where a suspending agent is required, but where high viscosity is either not required or presents a disadvantage. To be a useful product for most applications, however, the viscosity of low viscosity Xanthan gum must be restored to that of a normal xanthan gum produced by typical fermentation.

Publications which are considered pertinent are as follows:

1. P. Rogovin, et al. 1970. "Continuous Fermentations Produce Xanthan Biopolymer: Laboratory Investigations". Biotechnology and Bioengineering, 12, p. 75–83.
2. M. C. Cadmus, et al, 1978, "Synthetic Media for Production of Quality Xanthan Gum in 20 Liter Fermenters". Biotechnology and Bioengineering, 20, 1003–1014.
3. Process for Production of Xanthan Gum, British patent application No. 2,008,138 A. Tate and Lyle.

In the pertinent publications, medium formulations call for sulfate ion as a growth nutrient, but sulfate ion as producing reduced viscosity xanthan is not noted.

SUMMARY OF THE INVENTION

The invention comprises a process for production of heteropolysaccharides comprising culturing a microorganism of the genus Xanthamonas in a nutrient medium wherein the culturing is conducted in the presence of sulfate anion in a concentration effective for producing reduced viscosity heteropolysaccharide, relative to normal viscosity associated with a particular concentration of heteropolysaccharide.

SPECIFIC EMBODIMENTS OF THE INVENTION

It is known in the art that the pyruvate content of a heteropolysaccharide affects its viscosity. Further it is known that xanthan having a pyruvate content of less than 2% has a normal viscosity at xanthan concentrations greater than 0.25% but reduced viscosity at concentrations of less than 0.25% xanthan, when such viscosities are compared to high pyruvate-containing xanthan at similar concentrations.

The xanthan produced by the present invention, however, has a reduced viscosity compared to that of normal xanthan, at concentrations that range from 0.05% to 2%, thus far exceeding the low viscosity results of the low pyruvate containing xanthan gum.

The present invention is further illustrated by describing the culturing techniques which can be varied by those skilled in the art. Low viscosity xanthan of the present invention can be produced either by a batch mode in a shake flask culture or in a batch fermentor, or by continuous fermentation.

In a method utilizing the shake flask culture, a volume of nutrient medium is charged into a culture flask, sterilized, and inoculated with an active culture of a Xanthomonas species at a ratio of inoculum to medium of from about 1 to 10 to about 1 to 20. The flask is agitated to provide aeration to the culture, and the incubation temperature is controlled. Phosphate buffer, or another suitable buffer, is incorporated in the nutrient medium to maintain the culture pH above about 5.5. The incubation is continued for about 48 to 96 hours, or until the reaction is complete.

In a batch fermentation method, any conventional stirred tank batch reactor may be employed. The reactor may be outfitted for aseptic operation, agitation, aeration, temperature, and pH control, foam control, and measurement of dissolved oxygen. The reactor is charged with a desired volume of nutrient medium and sterilized. The fermentor is then seeded with an inoculum of culture at an inoculum level of between 5% and 10% of the nutrient medium volume.

The expression, "nutrient medium", as used in the present specification and claims is intended to mean a medium that contains in known or unknown compositions and proportions, essential mineral salts, trace elements, glucose or an equivalent carbohydrate and a source of nitrogen such as $NH_4Cl$ or $NH_4NO_3$, with or without supplemental organic growth factors. These growth factors include vitamins with or without appropriate amine acids. In the place of the above nitrogen sources, an undefined source thereof, such as yeast extract, yeast autolysate, dried distiler solubles (DDS), etc., may be employed.

In carrying out the batch fermentation method of the present invention, the following broad and preferred operating conditions are noted below.

| Agitation: | 1000 to 2000 rpm |
|---|---|
| Preferably: | 500 to 1000 rpm |
| Air Rate: | 0.2 to 2 vol/vol/min |
| Preferably: | 0.5 to 1 vol/vol/min |
| Temperature: | 20 to 35° C. |
| Preferably: | 25 to 30° C. |
| pH: | 5.5 to 8 |
| Preferably: | 6.4 to 7.4 |
| Dissolved Oxygen: | 10% to 90% saturation |
| Preferably: | 20% to 60% saturation |

In the continuous fermentation method, any conventional stirred tank continuous reactor may be employed. The tank should be provided for aseptic operation, agitation, aeration, temperature, and pH control, foam control, measurement of dissolved oxygen, and level control. The continuous process can be conducted in either a single-stage or two-stage continuous mode. In the single-stage continuous mode, the concentration of the biomass is set by the concentration of the limiting nutrient being fed with the medium and the biomass concentration can be varied by raising or lowering the limiting nutrient concentration. The growth limiting nutrients normally employed are nitrogen, phosphorus, and magnesium. Thus, the quantity of biomass obtained will be determined by the concentration of the limiting nutrient. A portion of the residual glucose or equivalent sugar present is converted to low viscosity xanthan gum, and the latter ultimately recovered from the fermentor effluent.

In a two-stage continuous mode, the ferment from a single-stage embodiment is taken to a second fermentation stage where additional glucose or equivalent sugar is introduced and converted to xanthan. In operation of the second stage, a balance of flow of the first-stage effluent and glucose solution must approximate the flow rate of the second-stage effluent.

In a continuous culture method, a nutrient medium to be employed is charged to the reactor and sterilized.

After seeding the medium with an innoculum of culture (usually 5% to 10% of the medium volume), the culture is allowed to grow in batch mode for approximately 24 to 48 hours until the desired cell concentration is reached. Continuous culture is initiated by pumping in fresh sterile medium at a desired flow rate and drawing off product at the same rate, based on an overflow level control device. The dilution rate (flow rate divided by the fermentor liquid volume) is set to be initially 75% of the maximum specified growth rate of a culture. After two culture turnovers (a turnover is the time required to completely replace one volume of broth in the fermentation vessel, or the reciprocal of the dilution rate), the dilution rate is set at the desired level.

In carrying out the continuous process, the following broad and preferred operating conditions are noted below:

| Dilution Rate: | 0.01–0.14 $hrs^{-1}$ |
|---|---|
| Preferably: | 0.04–0.1 $hrs^{-1}$ |
| Temperature: | 20–35° C. |
| Preferably: | 25–35° C. |
| pH: | 5.5–8.5 |
| Preferably: | 6.0–7.4 |
| Air Rate: | 0.2–2 vol/vol/min |
| Preferably: | 0.5–1 vol/vol/min |
| Agitation Rate: | 200–1200 rpm |
| Preferably: | 500–800 rpm |
| Dissolved $O_2$: | 10–90% of saturation |
| Preferably: | 20–60% of saturation |

Representative species of the Xanthomonas genus which may be used in carrying out this invention include *Xanthomonas carotae, Xanthomonas phaseoli, Xanthomonas papavericola, Xanthomonas begoniae, Xanthomonas agderae, Xanthomonas translucens, Xanthomonas vasculorum, Xanthomonas vesicatoria, Xanthomonas incanae,* and *Xanthomonas malvacearum,* as well as *Xanthomonas campestris.* Cultures of these organisms, as well as other of this genus may be obtained from the American Type Culture Collection in Rockville, Md.

The concentration of the sulfate ion in the medium should be an amount effective to produce reduced viscosity xanthan, and is measured in weight percent (wt %) of the nutrient medium. Tests have shown that a sulfate concentration of 0.05 wt % did not produce a low viscosity xanthan. It is believed a concentration above about 0.2 wt % is effective to result in reduced viscosity xanthan. Based on cost and possible poisoning of the culture, a concentration range of from about 0.2 to about 0.5 wt % is desirable. Preferably, this concentration ranges from about 0.3–0.4 wt %, and most preferably, the sulfate anion concentration is within the range of about 0.35 to about 0.38 wt %.

Any cation may be used with the sulfate anion, provided the sulfate salt is soluble in water and the cation is not toxic to the culture in the concentrations used. Sodium sulfate and ammonium sulfate have been found to work particularly well.

By comparison, the viscosity ratio of normal xanthan to low viscosity xanthan, both produced under similar conditions except for the addition of the sulfate anion to the low viscosity fermentation, ranges from 1.3:1 to 5:1.

EXAMPLE

A liquid nutrient medium having the composition listed in Table 1 was prepared.

TABLE 1

| Ingredient | Amount/Liter |
|---|---|
| Glucose | 25 gm |

TABLE 1-continued

| Ingredient | Amount/Liter |
| --- | --- |
| L-histidine .HCl | 1 mg |
| DL-methionine | 2 mg |
| DL-tryptophan | 2 mg |
| Biotin | 2 mcg |
| Cappantothenate | 400 mcg |
| Folic Acid | 2 mcg |
| Inositol | 2000 mcg |
| Niacin | 400 mcg |
| Paraminobenzoic Acid | 200 mcg |
| Pyridoxinel HCl | 400 mcg |
| Riboflavin | 200 mcg |
| Thiaamine HCl | 400 mcg |
| $H_3BO_3$ | 500 mcg |
| $CuSO_4$ | 400 mcg |
| KI | 100 mcg |
| $FeCl_3$ | 200 mcg |
| $MnSO_4$ | 400 mcg |
| $Na_2MoO_4$ | 200 mcg |
| $ZnSO_4$ | 400 mcg |
| $MgSO_4$ | 0.5 gm |
| NaCl | 0.1 gm |
| $CaCl_2$ | 0.1 gm |
| $K_2HPO_4$ | 6 gm |
| $KH_2PO_4$ | 1 gm |
| Distilled Water | 1000 ml |

An inoculum was prepared by growing the *Xanthomonas campestris* NRRL B-1459 from the Northern Regional Research Center of the U.S. Department of Agriculture, Peoria, Ill., for eighteen hours in YM broth at 28° C. in 500 ml of nutrient medium with additions as shown in Table 2 in the indicated numbered 2800 ml Fernbach flasks. The media were then sterilized, adjusted pH 7.2 and inoculated with 25 ml of the YM broth culture. The shake flasks were incubated at 28° C. on a shaker at 300 rpm for 96 hours.

TABLE 2

| Flask No. | L-Asparagine (gm) | $(NH_4)_2SO_4$ (gm) | Dry Distiller Solubles (gm) | Yeast Extract (gm) | $(NH_4)_2HPO_4$ (gm) | Urea (gm) | L-Aspartate | $NH_4Cl$ (gm) | $NaSO_4$ (gm) |
| --- | --- | --- | --- | --- | --- | --- | --- | --- | --- |
| 1 | 1.5 | 5.0 | — | — | — | — | — | — | — |
| 2 | — | — | 8.0 | — | — | — | — | — | — |
| 3 | — | — | — | 2.5 | — | — | — | — | — |
| 4 | — | — | — | — | 6.0 | 0.4 | — | — | — |
| 5 | 1.5 | 5.0 | — | — | — | — | — | — | — |
| 6 | 1.5 | 5.0 | — | — | — | — | — | — | — |
| 7 | 1.5 | 5.0 | — | — | — | — | — | — | — |
| 8 | 1.5 | — | — | — | — | — | — | — | — |
| 9 | 1.5 | 5.0 | — | — | — | — | — | — | — |
| 10 | 1.5 | 5.0 | — | — | — | — | — | — | — |
| 11 | — | — | 8.0 | — | — | — | — | — | — |
| 12 | — | 5.0 | — | — | — | — | — | — | — |
| 13 | 1.5 | — | 2.0 | — | — | — | — | — | — |
| 14 | — | 5.0 | — | — | — | — | 1.5 | — | — |
| 15 | 1.5 | — | — | — | — | 0.4 | — | — | — |
| 16 | 1.5 | — | — | — | 6.0 | — | — | — | — |
| 17 | 1.5 | — | — | — | — | 0.4 | — | — | — |
| 18 | 1.5 | — | — | — | — | 0.4 | — | — | 4.6 |
| 19 | — | — | — | — | — | 0.4 | — | 0.6 | — |
| 20 | — | — | — | — | — | 0.4 | — | 0.6 | 4.6 |
| 21 | — | 5.0 | 8.0 | — | — | — | — | — | — |
| 22 | — | — | 8.0 | — | — | — | — | — | 4.6 |
| 23 | — | — | 8.0 | — | — | — | — | — | — |
| 24 | — | 5.0 | — | — | — | 0.4 | — | — | — |

In Flasks 5 and 10, the vitamins were removed from the medium. In Flasks 6, 7, 8, and 9, distilled water was replaced with tap water.

Xanthan concentrations and viscosity were determined and are shown in Table 3. Viscosity was determined using a Brookfield Model LVT viscometer at 30 rpm and No. 4 spindle.

TABLE 3

| Flask No. | Viscosity (cp) | Xanthan Concentration (%) | Sulfate Presence | Low Viscosity Xanthan |
| --- | --- | --- | --- | --- |
| 1 | 1160 | 1.08 | Yes | Yes |
| 2 | 4020 | 1.08 | No | No |
| 3 | 2860 | 0.99 | No | No |
| 4 | 1720 | 0.70 | No | No |
| 5 | 2520 | 1.50 | Yes | Yes |
| 6 | 1640 | 1.17 | Yes | Yes |
| 7 | 2200 | 1.45 | Yes | Yes |
| 8 | 2940 | 1.09 | No | No |
| 9 | 1720 | 1.22 | Yes | Yes |
| 10 | 1740 | 1.28 | Yes | Yes |
| 11 | 4700 | 1.28 | No | No |
| 12 | 920 | 0.85 | Yes | Yes |
| 13 | 2480 | 0.93 | No | No |
| 14 | 1840 | 1.09 | Yes | Yes |
| 15 | 2660 | 0.99 | No | No |
| 16 | 2820 | 0.97 | No | No |
| 17 | 2260 | 0.94 | No | No |
| 18 | 1880 | 1.36 | Yes | Yes |
| 19 | 1480 | 0.70 | No | No |
| 20 | 1080 | 1.09 | Yes | Yes |
| 21 | 2200 | 1.23 | Yes | Yes |
| 22 | 2720 | 1.27 | Yes | Yes |
| 23 | 5260 | 1.28 | No | No |
| 24 | 1680 | 0.91 | Yes | Yes |

As is shown in Table 3, the viscosity of the xanthan gum is reduced by the addition of sufficient quantities of sulfate ion, either as a sodium or ammonium compound.

EXAMPLE 2

Flask numbers 1, 2, 4, 6, 9, 12, 16, and 24 produced in Example 1 were stored for approximately 60 days at 40° C. Initial viscosity for the xanthan contained in each flask is listed as determined in Example 1.

Each sample was heated to 90° C. for a period of 5 minutes. The sample was then allowed to cool to room temperature and subjected to a second viscosity determination as completed in Example 1. The results are shown in Table 4.

TABLE 4

| Flask No. | Initial Viscosity (cp) | Viscosity after Heating (cp) | Viscosity Increase (%) | Sulfate Present |
|---|---|---|---|---|
| 1 | 1160 | 2720 | 134 | Yes |
| 2 | 4020 | 4480 | 11 | No |
| 4 | 1720 | 2320 | 34 | No |
| 6 | 1640 | 3860 | 135 | Yes |
| 9 | 1720 | 4020 | 134 | Yes |
| 12 | 920 | 2040 | 121 | Yes |
| 16 | 2820 | 4160 | 47 | No |
| 24 | 1680 | 3640 | 117 | Yes |

As shown by the results, example samples having sulfate present during fermentation exhibited a viscosity increase ranging from 117 to 135% whereas samples with no sulfate present during fermentation exhibited increases ranging from 11 to 54%.

I claim:

1. A process for the production of a heteropolysaccharide comprising culturing a microorganism of the genus Xanthomonas in a nutrient medium containing sulfate anion in a concentration effective to produce reduced viscosity heteropolysaccharide, said concentration being above about 0.2 wt %.

2. A process for production of a heteropolysaccharide comprising culturing a microorganism of the genus Xanthomonas in a nutrient medium contained in a fermentation zone, said nutrient medium containing sulfate anion in a concentration effective to produce reduced viscosity xanthan, said concentration being above about 0.2 wt %; withdrawing a heteropolysaccharide containing effluent from said zone; and heating said heteropolysaccharide containing effluent.

3. A process for production of heteropolysaccharide comprising continuously culturing a microorganism of the genus Xanthomonas in a nutrient medium contained in a fermentation zone, said nutrient medium containing sulfate anion in a concentration effective to produce reduced viscosity xanthan, said concentration being above about 0.2 wt %; and withdrawing a heteropolysaccharide containing effluent from said zone while continuing said culturing in said zone at a rate such that an essentially steady-state condition is maintained.

4. A process for production of heteropolysaccharide comprising continuously culturing a microorganism of the genus Xanthomonas in a nutrient medium contained in a fermentation zone, said nutrient medium containing sulfate anion in a concentration effective to produce reduced viscosity xanthan, said concentration being above about 0.2 wt %; withdrawing a heteropolysaccharide containing effluent from said zone while continuing said culturing in said zone at a rate such that an essentially steady-state condition is maintained; and heating said withdrawn heteropolysaccharide containing effluent.

5. A process for the production of heteropolysaccharide comprising culturing a microorganism of the genus Xanthomonas in a nutrient medium, containing sulfate anion having a concentration ranging from about 0.2 to about 0.5 wt %.

6. A process for production of a heteropolysaccharide comprising culturing a microorganism of the genus Xanthomonas in a nutrient medium contained in a fermentation zone, said nutrient medium containing sulfate anion having a concentration ranging from about 0.2 to about 0.5 wt %; withdrawing a heteropolysaccharide containing effluent from said zone; and heating said heteropolysaccharide containing effluent.

7. A process for production of heteropolysaccharide comprising continuously culturing a microorganism of the genus Xanthomonas in a nutrient medium contained in a fermentation zone, said nutrient medium containing sulfate anion having a concentration ranging from about 0.2 to about 0.5 wt %; and withdrawing a heteropolysaccharide containing effluent from said zone while continuing said culturing in said zone at a rate such that an essentially steady-state condition is maintained.

8. A continuous process for production of a heteropolysaccharide comprising continuously culturing a microorganism of the genus Xanthomonas in a nutrient medium contained in a fermentation zone, said nutrient medium containing sulfate anion having a concentration ranging from about 0.2 to about 0.5 wt %; withdrawing a heteropolysaccharide containing effluent from said zone while continuing said process in said zone at a rate such that an essentially steady-state condition is maintained; and heating said withdrawn heteropolysaccharide containing effluent.

9. The process of claim 5, 6, 7, or 8 in which the sulfate anion concentration ranges from about 0.3 to about 0.4 wt %.

10. The process of claim 5, 6, 7, or 8 wherein th sulfate anion concentration ranges from about 0.35 to about 0.38 wt %.

11. The process of claim 5, 6, 7, or 8 wherein said nutrient medium contains essentially glucose, mineral salts, $NH_4Cl$, and a mixture of vitamins.

12. The process of claim 1, 2, 3, 4, 5, 6, 7, or 8 wherein the heteropolysaccharide is xanthan.

* * * * *